United States Patent [19]

Lee et al.

[11] Patent Number: 5,774,217
[45] Date of Patent: Jun. 30, 1998

[54] MEASUREMENT OF NONLINEAR REFRACTIVE INDEX COEFFICIENT OF OPTICAL FIBER BY SAGNAC INTERFEROMETER

[75] Inventors: Hak-Kyu Lee; Kyong-Hon Kim; Seo-Yeon Park; El-Hang Lee, all of Daejeon, Rep. of Korea

[73] Assignee: Electronics and Telecommunications Research Institute, Daejeon, Rep. of Korea

[21] Appl. No.: 734,265

[22] Filed: Oct. 21, 1996

[30] Foreign Application Priority Data

Nov. 17, 1995 [KR] Rep. of Korea ................... 1995-42069

[51] Int. Cl.[6] .......................................................... G01B 9/02
[52] U.S. Cl. .......................................... 356/350; 356/361
[58] Field of Search ..................................... 356/361, 350, 356/345; 385/12, 15, 31; 250/27, 51, 227.14, 227.27, 227.19

[56] References Cited

U.S. PATENT DOCUMENTS 4,875,775 10/1989 Michal et al. ........................... 356/350
5,357,333 10/1994 DeBernardi et al. ................... 356/361

FOREIGN PATENT DOCUMENTS

0685722A2 12/1995 European Pat. Off. .

OTHER PUBLICATIONS

Measurement of the nonlinear index of silica–core and dispersion–shifted fibers; K.S. Kim, R. H. Stolen, W.A. Reed and K.W. Quoi; Feb. 15, 1994; pp. 257–259.

Measurement of Fiber Nonlinear Kerr Coefficient by Four--Wave Mixing; L. Prigent and J.P. Hamaide; Sep. 1993; pp. 1092–1095.

*Primary Examiner*—Frank G. Font
*Assistant Examiner*—Jason D. Vierra-Eisenberg
*Attorney, Agent, or Firm*—Antonelli, Terry, Stout & Kraus, LLP

[57] ABSTRACT

A measurement of nonlinear refractive index coefficient of an optical fiber with a Sagnac interferometer, comprises the steps of employing the optical fiber in a Sagnac interferometer, splitting a signal beam into two signals, launching the two split signals into the interferometer in opposite directions, combining and detecting the signals counter-propagated in the interferometer, and detecting the refractive index coefficient of the optical fiber in accordance with the difference between the two signal powers determined by a control beam. The quasi-static phase shift of the signal beam counter-propagating the same paths of the interferometer is induced by rotating the optical fiber loop of the interferometer. The present invention gives rise to little error because it does not require precise information about the pulse width of a used beam or a high-power light.

3 Claims, 5 Drawing Sheets

0π

π

1.5π

3.5π

MEASUREMENT OF NONLINEAR REFRACTIVE INDEX COEFFICIENT OF OPTICAL FIBER BY SAGNAC INTERFEROMETER

BACKGROUND OF THE INVENTION

1. Field of the Invention

The present invention relates to a measurement of nonlinear refractive index coefficient of an optical medium by Sagnac interferometer and, more particularly, to a measurement of the nonlinear refractive index which is suitable for a medium of a long nonlinear interaction length, such as an optical fiber.

2. Discussion of Related Art

Generally, the term "nonlinear optical effect" refers to a phenomenon that the refractive index of a medium in use changes according to the power of an incident beam. With the advance of lasers and light amplifiers, the power of light became stronger than ever, and now the resultant nonlinear optical effect causes various phenomena.

For example, an optical fiber has a typical core diameter of several micrometers, so that the power of light signal per unit area is very high. Since optical fibers also have an inherent long path length for light signals, the length for nonlinear optical interaction becomes very long and thus, the nonlinear optical effect is easily observed in optical fibers.

However, this nonlinear optical effect is a dominant factor inducing cross-talk between light signals in high-speed optical communications and gives rise to limitations on the distance between amplifiers in a long-distance optical communication systems by cable.

Thus, the nonlinear refractive index coefficient must be precisely determined for the design of communication systems.

For the conventional measurement techniques for a nonlinear refractive index coefficient of an optical fiber, self-phase modulation and four-phase mixing have been applied.

Although the experimental configuration is simple in self-phase modulation, other nonlinear optical effects may be induced due to the use of high power light and it requires the knowledge of an exact pulse width.

On the other hand there is no need to measure the pulse width of the light in four-wave mixing due to the use of continuous radiation rather than pulse radiation. But it requires that phase matching be precisely achieved.

FIG. 1 is an experimental configuration for measuring the nonlinear refractive index coefficient of an optical fiber by using conventional self-phase modulation method, which comprises a pulse laser 1 for providing radiation of great peak power, an optical isolator 2 for fixing light signals in one direction, an optical fiber 3, of which the nonlinear refractive index is to be measured, connected to the optical isolator so as to receive and transmit the light signals, and a scanning Fabry-Perot interferometer 4 for analyzing the spectrum of the light signal coming out of the optical fiber 3.

The measurement of nonlinear refractive index of an optical fiber using self-phase modulation method of the prior art in FIG. 1 is described as follows.

Nonlinear refractive index induced by light, which is proportional to the power of the light beam and nonlinear refractive index coefficient, affects itself. In other words, the phase distribution in time domain while the light's travelling on an optical fiber depends on its power distribution.

If the phase distribution in time domain is fourier transformed, the resulting distribution in frequency domain shows several peaks proportional to the light power and the magnitude of a nonlinear refractive index coefficient.

FIGS. 2A through 2D are distribution diagrams for pulse signals in a frequency domain during the measurement of the nonlinear refractive index coefficient by self-phase modulation method.

The self-phase modulation method is a technique for modulating the power of an incident beam so as to obtain an already known waveform in a frequency domain and measuring the beam power at that time so as to calculate a proportional constant, nonlinear refractive index coefficient.

Though the experimental configuration of self-phase modulation is relatively simple, beam powers strong enough to induce nonlinear phase shift over $\pi$ is required so as to discriminate the resultant waveform from others because the phase shift might be measured with the waveform in a frequency domain.

However, the high-powered beam may be additionally ready to induce other nonlinear effects such as SRS, SBS, four-wave mixing and the like, thus special attention will be paid to the unavoidable effects through careful measurement.

For the calculation of nonlinear refractive index, the exact peak power must be measured and the average peak power is computed and then divided by repetition rate and FWHM. The knowledge of a precise waveform is required to obtain exact FWHM.

In conclusion, there are many potential sources for errors in the measurement of nonlinear refractive index by self-phase modulation.

FIG. 3 illustrates an experimental configuration for measuring the nonlinear refractive index of an optical fiber by conventional four-wave mixing method, which comprises first and second lasers 11 and 12 for sources of radiation, first and second polarizers 13 and 14 for receiving and selectively polarizing the laser beam, an optical fiber 15 of which the nonlinear refractive index coefficient is to be measured, a coupler 16 for launching the laser beam into the optical fiber 15, and a spectrometer 17 for receiving the output signal from the optical fiber 15 and analyzing the spectrum of the signal.

Nonlinear optical effects cause the mutual interaction of several incident beams in an optical fiber and generate a new signal having a frequency corresponding to the sum or remainder of the incident beams.

In particular a nonlinear refractive index coefficient $n_2$ causes four-wave mixing, which is a phenomenon in which a fourth beam is generated with three incident beams.

Since the nonlinear refractive index coefficient of a medium is proportional to the power of the fourth beam, it might be computed by obtaining the power of the fourth beam and those of the other three beams at once.

FIGS. 4A and 4B are power distribution diagrams for signals in a frequency domain during the measurement of the nonlinear refractive index coefficient by the four-wave mixing method.

With reference to these figures, a frequency component $\lambda_3$ is formed with the interaction of two $\lambda_2$ and one $\lambda_1$, while $\lambda_4$ is formed with the interaction of two $\lambda_1$ and one $\lambda_2$. In four-wave mixing measurement, it is relatively free from errors which might be caused by the indispensable measurement of FWHM of pulse in self-phase modulation method, because only the knowledge of the average power is needed.

However, we have to meet the need of precise phase matching in four-wave mixing measurement so as to get an effective fourth wave.

SUMMARY OF THE INVENTION

Accordingly, the present invention is directed to a measurement of the nonlinear refractive index coefficient of optical medium by utilizing a Sagnac interferometer that substantially obviates one or more of the problems due to limitations and disadvantages of the related art.

The object of the present invention is to provide an instrument for measuring the nonlinear refractive index coefficient of an optical fiber which gives rise to little error because it requires no precise information about the pulse width of a used beam and no high-power light.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, a Sagnac interferometer is used for a phase-power transformer that transforms a phase shift in the interferometer into a power shift. A general interferometer is an optical instrument for measuring the interference pattern or the degree of interference by splitting an incident beam into two beams, leading the respective split beams into two different paths and combining them.

A Sagnac interference path has two identical interference arms, so that it is a most stable structure against outer environments such as temperature or vibration.

The measuring instrument for nonlinear refractive index coefficient of an optical fiber by a Sagnac interferometer of the present invention comprises a fiber coupler for splitting an incident beam into two beams having different paths, an optical fiber of which the nonlinear refractive index coefficient is to be measured, a Sagnac interferometer employing an optical fiber loop for making the two split signal beams counter-propagate the optical fiber, a first wavelength division multiplexeing coupler for launching a control beam into the Sagnac interferometer, a second wavelength division multiplexing coupler for extracting the control beam from the Sagnac interferometer, a detector for detecting an output signal beam which is composed of two beams counter-propagated through the optical fiber loop and being combined by the multiplexing coupler, a lock-in amplifier for amplifying and phase-sensitive measuring the output signal beam, and a swing device for rotating the optical fiber to induce a quasi-static phase shift in the signal beams counter-propagating the optical fiber.

In the principle of the present invention as described above, the optical fiber is placed in the Sagnac interferometer and the control beam is launched into the interferometer so as to induce a nonlinear refraction, which brings about an output phase shift according to the principle of an interferometer. The phase shift has respect to the nonlinear refractive index coefficient of an optical fiber and the power of initial control beam. Therefore, the nonlinear refractive index coefficient is calculated by measuring the output power and the initial control pulse power.

It is to be understood that both the foregoing general description and the following detailed description are exemplary and explanatory and are intended to provide further explanation of the invention as claimed.

BRIEF DESCRIPTION OF THE ATTACHED DRAWINGS

The accompanying drawings, which are included to provide a further understanding of the invention and are incorporated in and constitute a part of this specification, illustrate embodiments of the invention and together with the description serve to explain the principles of the drawings.

DETAILED DESCRIPTION OF PREFERRED EMBODIMENT

Reference will now be made in detail to the preferred embodiments of the present invention, examples of which are illustrated in the accompanying drawings.

Figure 1:
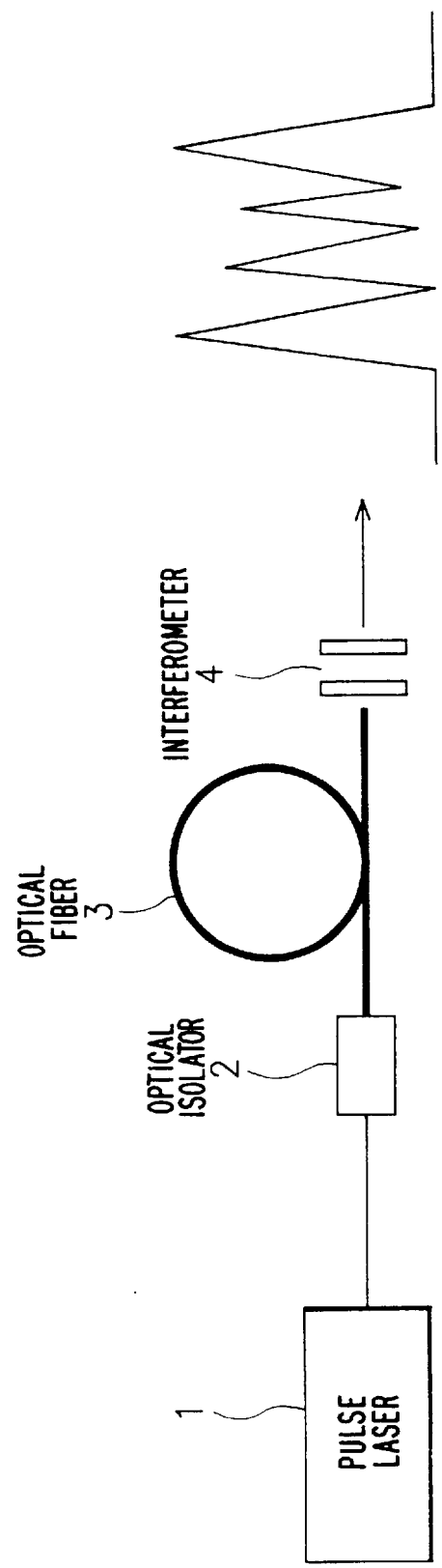
FIG. 1 is an experimental configuration for measuring the nonlinear refractive index coefficient of an optical fiber by conventional self-phase modulation method.
Figure 2A:
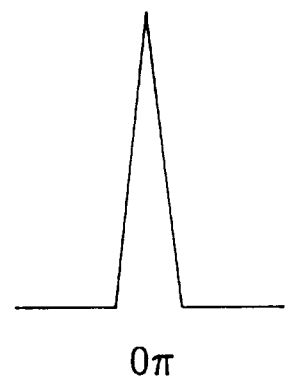
FIGS. 2A through 2D are power distribution diagrams for pulse signals in a frequency domain during the measurement of the nonlinear refractive index coefficient by self-phase modulation method.
Figure 2B:
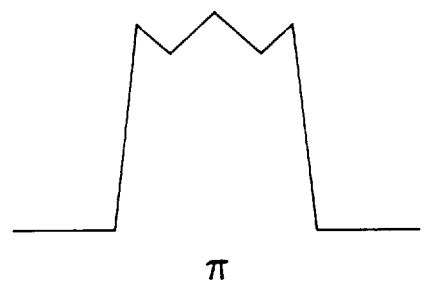
Figure 2C:
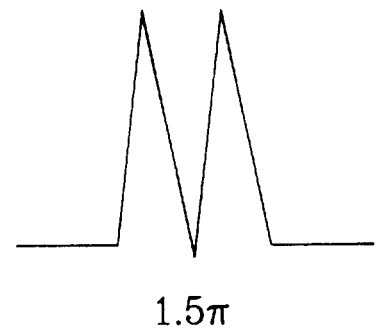
Figure 2D:
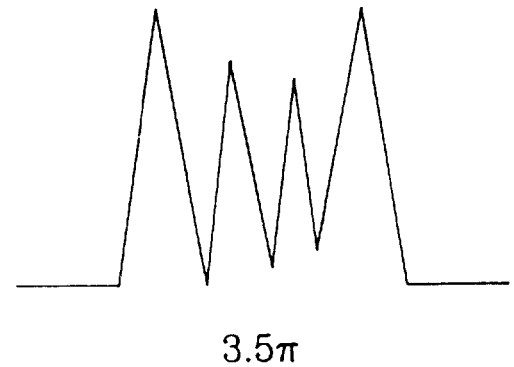
Figure 3:
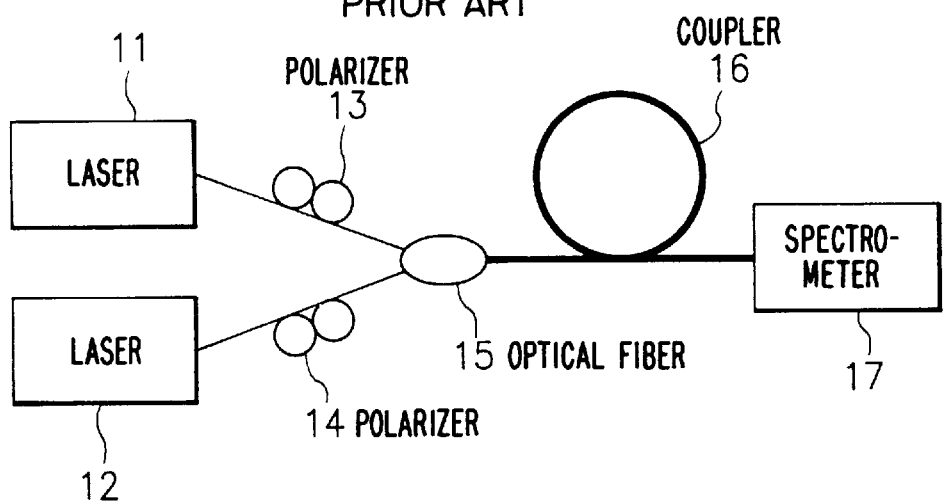
FIG. 3 is an experimental configuration for measuring the nonlinear refractive index coefficient of an optical fiber by conventional four-wave mixing method.
Figure 4A:
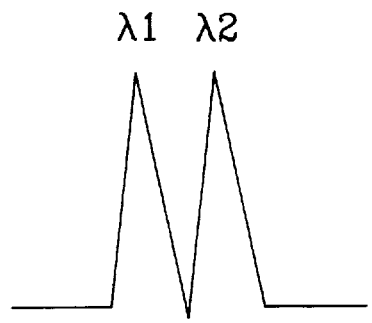
FIGS. 4A and 4B are power distribution diagrams for signals in a frequency domain during the measurement of the nonlinear refractive index coefficient by four-wave mixing method.
Figure 4B:
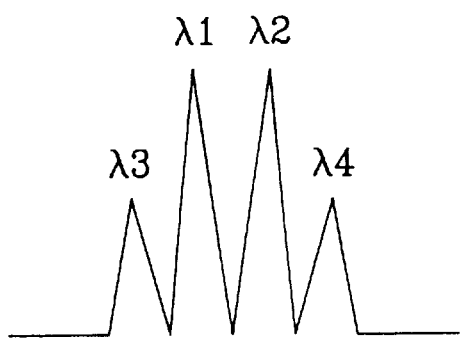
Figure 5:
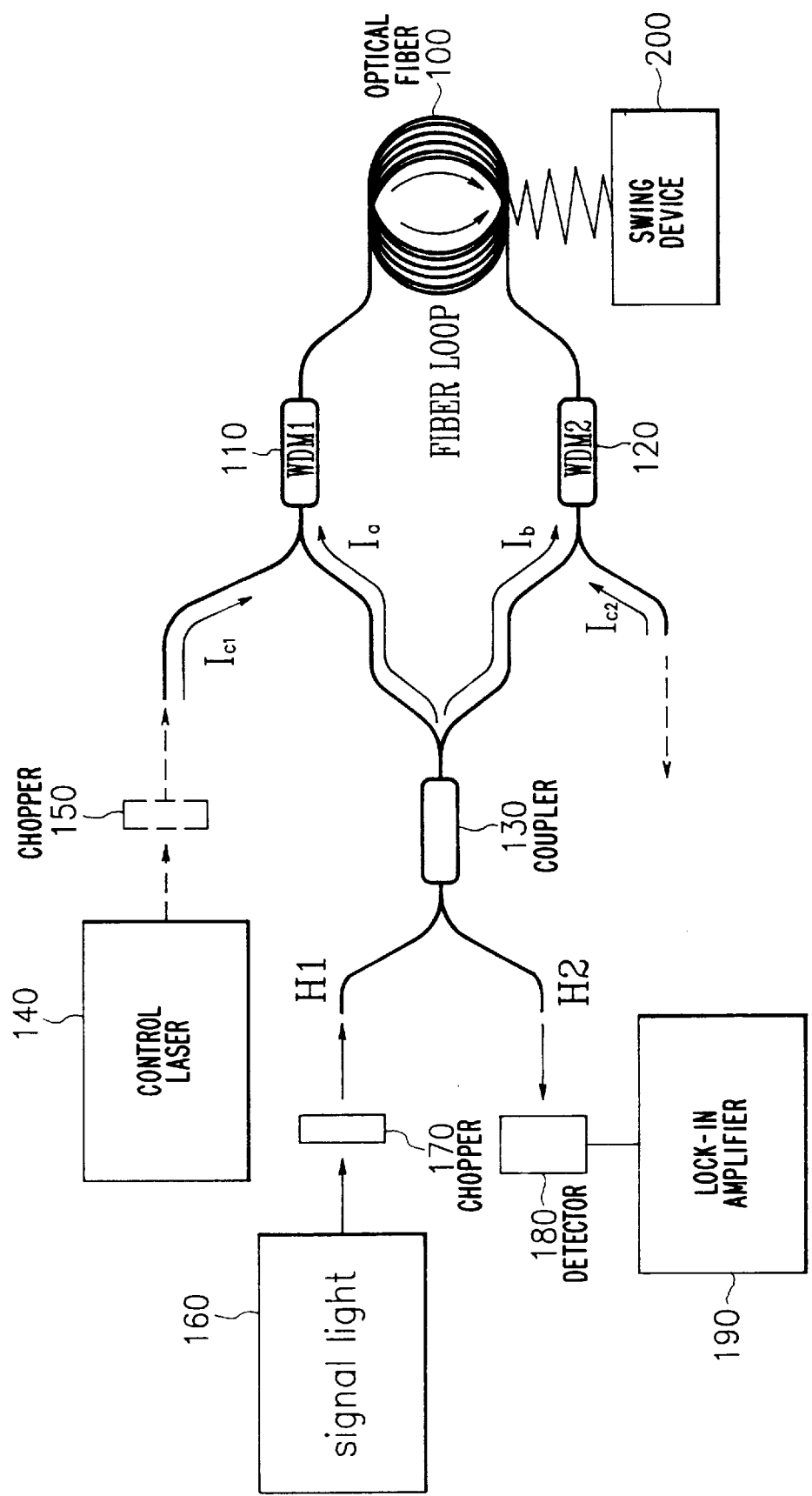
FIG. 5 is an experimental configuration for measuring the nonlinear refractive index coefficient of an optical fiber by using a Sagnac interferometer according to the present invention.

FIG. 5 is a construction view of an experimental configuration for measuring nonlinear refractive index coefficient of an optical fiber with a Sagnac interferometer according to the present invention.

The experimental setup of FIG. 5 comprises a first chopper 170 for receiving a signal beam from a signal laser 160, 3-dB fiber coupler 130 for splitting the signal beam from the first chopper 170 into 50:50 so as to launch into an interferometer through two different paths, respectively, combining the two beams having traveled in opposite directions in the interferometer and transmitting the combined beam outside the interferometer, a second chopper 150 for receiving a control beam from a control laser 140, a first wavelength division multiplexing coupler (WDM1) 110 for launching one signal beam split by the 3-dB fiber coupler in one direction and the control beam from the first chopper 170 into an optical fiber 100 of which the nonlinear relative index coefficient is to be measured, and launching the other signal beam which was split by the multiplexing coupler 130 and having travelled the optical fiber 100 in the opposite direction into the multiplexing coupler 130, a swing device 200 for swinging the optical fiber 100, a second wavelength division multiplexing coupler (WDM2) 120 for separating the control beam out of the light signals which were launched into the optical fiber 100 by the WDM1 110, and launching the signal beam which were split by the 3-dB fiber coupler 130 and having travelled the other path into the optical fiber 100 in the opposite direction, a detector 180 for detecting the output signal beam which travelled the optical fiber 100 in opposite directions and combined in the 3dB fiber coupler 130, and a lock-in amplifier 190 for determining the power of the light signals detected by the detector 180.

The present invention is characterized by a 3-dB fiber coupler 130 for splitting an incident beam 50:50, a Sagnac interferometer which employs an optical fiber loop for making the two split signal beams counter-propagate the optical fiber 100, a first wavelength division multiplexing coupler (WDM1) 110 for launching a control beam into the Sagnac interferometer, a second wavelength division multiplexing coupler (WDM2) 120 for extracting the control beam from the Sagnac interferometer, a swing device 200 for rotating the optical fiber 100, a detector 180 and a lock-in amplifier 190.

Each first and second wavelength division multiplexing coupler 110 and 120 has the combination to split ratio of 100:0 and 0:100 for the wavelengths of control and signal beams, respectively. The signal beam is, therefore, by-passed without reserve, and the control beam is launched into the interferometer by the first wavelength division multiplexing coupler 110 and comes out of the interferometer by the second wavelength division multiplexing coupler 120.

The output signal power I at the interferometer transmission port H2 is given by $$I = \frac{I_s}{2}[1 - \cos(\Delta\phi + \Phi)] \quad (1)$$

where:

$I_s$ is the input signal power;

$\phi$ is the irreversible phase shift; and $\Delta\phi = \phi_a - \phi_b$, which is the phase difference between the two signals $I_a$ and $I_b$ counter-propagated in the interferometer, and $\phi_a$ and $\phi_b$ are values of phase terms corresponding to $I_a$ and $I_b$, respectively, during their transmission through the optical fiber loop.

the nonlinear phase shift induced on the signal power $I_a$ propagating with the control beam is equal to the accumulation of nonlinear refraction over the path length, which is represented numerically by the integration of the nonlinear refraction over the path length.

The nonlinear phase shift induced on the other signal power $I_b$ counter-propagating with respect to the control beam comes from averaging over the power of the control beam.

Consequently, the relationship between the radiant power of the beam incident upon the interferometer $I_o$ and the interferential power of the beam out of the interferometer I can be given by $$I = \frac{I_s}{2}\left[1 - \cos\left\{\frac{4\pi n_2}{\lambda_s A_{eff}}\left(\int_0^L I_c(t - \tau z e^{-dz} dz - \langle I_p \rangle L_{eff})\right)\right\}\right] \quad (2)$$

where:

$\lambda_s$ is the signal wavelength;

$n_2$ is the nonlinear refractive index coefficient of an optical fiber;

$\alpha$ is the linear loss of an optical fiber;

$A_{eff}$ is the effective core area of an optical fiber;

$I_p(t)$ is the control power pulse profile in time domain;

$\langle I_p \rangle$ is the average control pulse power;

L is the length of the optical fiber;

$$L_{eff} = \frac{(1 - e^{-dt})}{a}$$

$$\tau = \frac{1}{v_p} - \frac{1}{v_s}$$

$v_p$ and $v_s$ are the velocities of the signal beam and the control beam in an optical fiber, respectively; and $\Phi$ is the dc phase off-set within the interferometer.

$\phi_a$, the phase shift of $I_a$, is not merely proportional to the length of the optical fiber mediating the mutual interaction between the signal beam and the control beam, but is saturated according to the length. The magnitude of the saturation may be given by $$\Delta\phi_{ps} = \frac{4\pi}{\lambda_s} n_2 I_c \frac{\Delta t_0}{\tau} \quad (3)$$

where:

$\Delta t_o$ is the pulse width of the control beam;

$\lambda_s$ is the signal wavelength;

$I_c$ is the peak power of the control beam; and $\tau$ is the walk-off time between the signal beam and the control beam per unit length.

$\phi_a$ is represented in a square form of which the height is $\Delta\phi_1$ and half the width is equal to $\tau L$.

In measurement of these signals with a detector of low-speed response, the equation (2) must be averaged, which is given by $$\langle I \rangle = \frac{I_s}{2}(1 - \cos\Phi) - \frac{I_s}{4k^2}\langle I_p \rangle^2 \left(L_{eff}^2 - \frac{TL_{eff}}{\tau}\right)\cos\Phi \quad (4)$$

The above equation (4) consists of nonlinear and linear components according to whether or not the output power of the interferometer depends on the control pulse power respectively.

The size of the two components might be compared by substituting commonly used experimental variables, where the signal power $I_s$ is 1 mW, the average control pulse power $\langle I_p \rangle$ is about 10 mW, the constant k containing nonlinear refractive index is $10^{-3}$ W/m, the length of the optical fiber $L_{eff}$ is 1 km, the period of the control beam T is 10 ns and the walk-off time between the signal beam and the control beam $\tau$ is about 1 ns/km. The linear component is 1 mW but the nonlinear component is about $10^3$ mW, so that the linear component is much smaller than the nonlinear dc off-set.

For this reason, a phase-sensitive detector using a lock-in amplifier 190 is needed for the measurement of ac signal given with a large dc component.

After switching on or off the control beam incident upon the chopper 150 with a low frequency $\omega_{96}$ of about 100 Hz, the beam amplified by the lock-in amplifier 190 may be measured, and the value R is represented in the form $$R = \frac{1}{4}\langle I_p \rangle^2 k^2 \left(\frac{TL'_{eff}}{\tau} - L_{eff}^2\right) I_s |\cos\Phi| \quad (5)$$

When a slow phase shift $\phi_r$ is applied inside the interferometer, the dc phase off-set $\Phi$ is given by $$\Phi = \phi_r + \phi_i$$

here, $\phi_i$ is an irreversible phase shift which is not balanced in the Sagnac interferometer. In the process of irreversible phase shift occurring in the Sagnac interferometer, there are magnetic, time-varying and relativity phenomena.

Also, for a rotational sensitive interferometer, a Sagnac interferometer is rotated at speed of $\Omega$, the resultant phase shift is given by $$\Phi_\Omega = \frac{2\pi LD}{\lambda c} \Omega$$

Here C is the light velocity in the optical fiber, and D is the diameter of a spool wound with the optical fiber.

After a repetitive variation of the angular velocity from 0 to $\Omega$ with a period of $\Delta$ seconds, $\phi_r$ is determined by $$\Phi_r = -\frac{2\pi LD\Omega}{\lambda c} \frac{t}{\Delta} \quad -\Delta \leq t \leq 0$$

$$= \frac{2\pi LD\Omega}{\lambda c} \frac{t}{\Delta} \quad 0 \leq t \leq \Delta$$

The output from the lock-in amplifier in the above equation (5) varies depending on $\phi_r$, and R periodically varies from the value $R(\phi=\pi)$ to $R(\phi=\pi/2)$ after $\phi_\Omega$ exceeds $\pi$. The difference $\Delta R$ between $R(\phi=\pi)$ and $R(\phi=\pi/2)$ is equal to the difference between the maximum and the minimum of output power amplified by the lock-in amplifier, which is given by $$\Delta R = R(\Phi=\pi) - R\left(\Phi=\frac{\pi}{2}\right) \quad (6)$$

$$= \frac{1}{4} <I_P>^2 k^2 \left(\frac{TL_{eff}}{\tau} - L_{eff}^2\right) I_s$$

If the signal beam is modulated with a low frequency $\Omega_r$ by the former chopper without using the control beam, the output power R' amplified by the lock-in amplifier is given by the following equation due to the resultant quasi-static phase shift $\phi_r$ induced by the Sagnac effect as in the modulation of the control beam.

$$R = \frac{I_s}{2}(1-\cos\Phi) \quad (7)$$

Therefore, the difference between the maximum and the minimum of R, $\Delta R'$ is given by $$\Delta R'=R(\Phi=\pi)-R(\Phi=0)=I_s \quad (8)$$

Figure 6A:
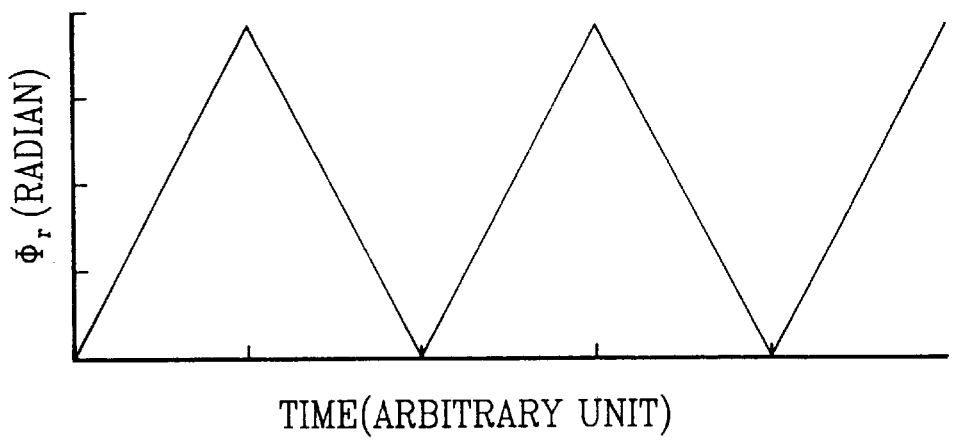
FIGS. 6A, 6B and 6C are power distribution diagrams for signals amplified with a lock-in amplifier in time domain during the measurement of the nonlinear refractive index coefficient by using a Sagnac interferometer according to the present invention.
Figure 6B:
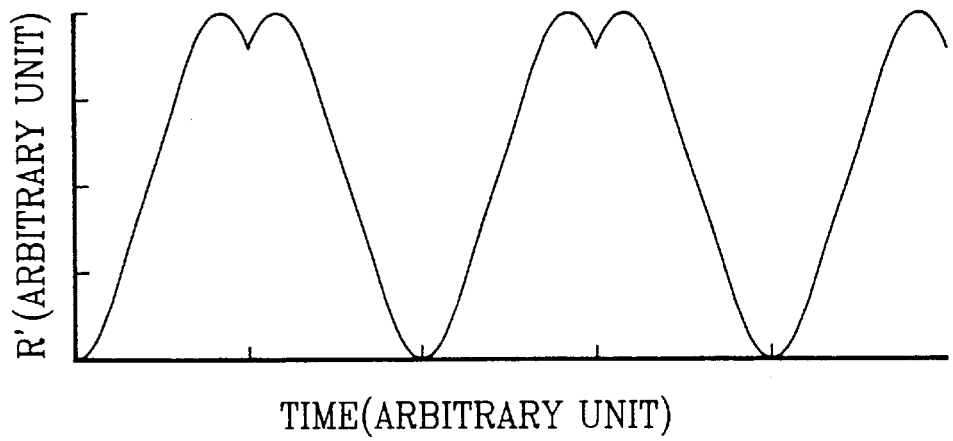
Figure 6C:
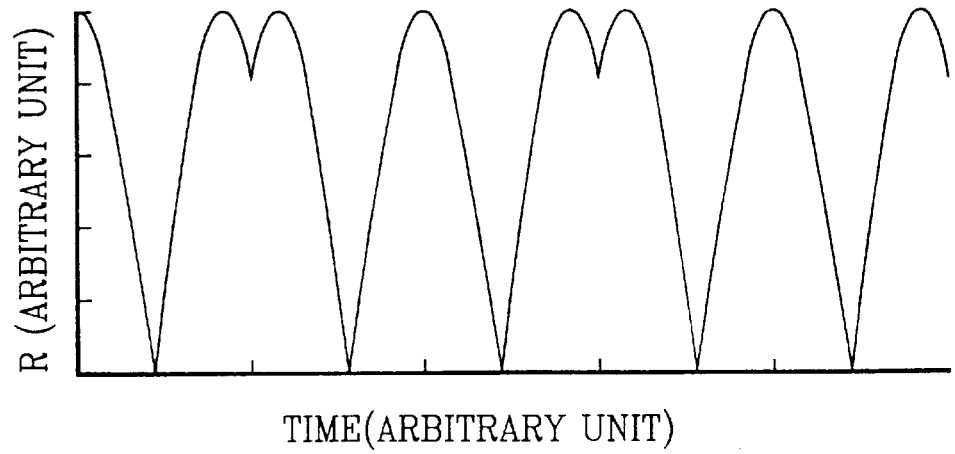

FIGS. 6A and 6B are power distribution diagrams in time domain for signals amplified with a lock-in amplifier during the measurement of the nonlinear refractive index coefficient by using a Sagnac interferometer, which illustrate waveforms in case of a phase shift $\phi_r$ from 0 to 1.2$\pi$.

When $\Delta R$ of the above equation (6) is divided by $\Delta R'$ of another equation (8), the result is written in the form $$\frac{\Delta R}{\Delta R'} = \frac{1}{4} k^2 \left(\frac{TL'_{eff}}{\tau} - L_{eff}^2\right) <I_P>^2$$

$$= \frac{1}{4} \left(\frac{4\pi n_2}{\lambda_s A_{eff}}\right)^2 \left(\frac{TL'_{eff}}{\tau} - L_{eff}^2\right) <I_P>^2$$

where, $\Delta R$ and $\Delta R'$ are directly measured by means of the amplitude modulated by a lock-in amplifier, and $n_2$ might be represented with measurable experimental parameters as follows.

$$n_2 = \frac{\lambda_s A_{eff}}{2\pi <I_P> L_{eff}} \left[\frac{\Delta R}{\Delta R'} \frac{1}{1-\frac{TL'_{eff}}{\tau L_{eff}^2}}\right]^{\frac{1}{2}}$$

In the measurement of nonlinear refractive index coefficient the thermal effect may be attended with the use of a high-power control beam and nonlinear optical effect may have an adverse affect, but the measuring instrument of the present invention enables us to obtain more accurate values than those measured with conventional techniques. Besides, the measurement may be performed only for obtaining the nonlinear refractive index coefficient by adequately regulating the length of the interferometer when a minute phase shift occurring in the interferometer is measured, which is helpful for respectively measuring the values when there are two nonlinear effects of different response times.

Thus, the present invent has advantages in that it is unnecessary to know the pulse width owing to an adequate modulation of the interferometer, a high-power beam is not used, and it enables the measurement of only nonlinear refractive index coefficient of an optical fiber which is troublesome in high-speed optical communication because it is not required to meet the need of phase matching. Moreover, the present invention might be applied to the fabrication of devices utilizing the nonlinear effects of an optical fiber such as an optical fiber switch, and it reduces accidental errors in measurement by inducing a quasi-static phase shift by means of the rotational sensitivity of a Sagnac interferometer.

It will be apparent to those skilled in the art that various modifications and variations can be made in the measurement of nonlinear refractive index coefficient of an optical fiber by Sagnac interferometer according to the present invention without departing from the spirit or scope of the invention. Thus, it is intended that the present invention cover the modifications and variations of this invention provided they come within the scope of the appended claims and their equivalents.

What is claimed is:

1. A method of measuring nonlinear refractive index coefficient of an optical fiber in a Sagnac interferometer, said method comprising the steps of:

employing said optical fiber in said Sagnac interferometer;

splitting a signal beam into two signals;

launching said two split signals into said interferometer in opposite directions;

combining and detecting said two split signals counter-propagating said interferometer; and determining the refractive index coefficient of said optical fiber in accordance with the different between the powers of said two split signals discriminated by a control beam;

wherein the phase shift of said two split signal beams counter-propagating the same paths of said interferometer is induced in a quasi-static state by rotating the optical fiber loop of said interferometer.

2. The measuring method defined in claim 1, wherein the phase shift of said output signal beam is measured by a phase-sensitive measurement with a lock-in amplifier.

3. An apparatus for measuring nonlinear refractive index coefficient of an optical fiber by utilizing a Sagnac interferometer, said apparatus comprising:

a 3-dB fiber coupler for splitting an incident beam into two split beams having different paths;

an optical fiber whose nonlinear refractive index coefficient is to be measured;

a Sagnac interferometer including said optical fiber loop for making the two split signal beams counter-propagate said optical fiber;

a swing device for rotating said optical fiber causing a quasi-static phase shift of the signal beams counter-propagating said optical fiber:

a first wavelength division multiplexing coupler for launching a control beam into said Sagnac interferometer;

a second wavelength division multiplexing coupler for extracting said control beam from said Sagnac interferometer;

a detector for detecting an output signal beam which is composed of the two split beams, the two split beams counter-propagating said optical fiber loop and being combined by said 3-dB fiber coupler;

a lock-in amplifier for amplifying and measuring the power of said output signal beam.

* * * * *